United States Patent
Zhang et al.

(10) Patent No.: US 11,986,180 B2
(45) Date of Patent: *May 21, 2024

(54) ADJUSTABLE SUTURE LOCKING APPARATUS

(71) Applicant: Hangzhou Valgen Medtech Co., Ltd., Hangzhou (CN)

(72) Inventors: Weiwei Zhang, Hangzhou (CN); Tingchao Zhang, Hangzhou (CN); Xianzhang Zheng, Hangzhou (CN)

(73) Assignee: HANGZHOU VALGEN MEDTECH CO., LTD., Hangzhou (CN)

( * ) Notice: Subject to any disclaimer, the term of this patent is extended or adjusted under 35 U.S.C. 154(b) by 743 days.

This patent is subject to a terminal disclaimer.

(21) Appl. No.: 16/975,612

(22) PCT Filed: May 22, 2019

(86) PCT No.: PCT/CN2019/087885
§ 371 (c)(1),
(2) Date: Aug. 25, 2020

(87) PCT Pub. No.: WO2019/233278
PCT Pub. Date: Dec. 12, 2019

(65) Prior Publication Data
US 2021/0000464 A1    Jan. 7, 2021

(30) Foreign Application Priority Data

Jun. 8, 2018 (CN) .......................... 201810587805.9
Jun. 8, 2018 (CN) .......................... 201820892356.4

(51) Int. Cl.
*A61B 17/04* (2006.01)
*A61B 17/00* (2006.01)

(52) U.S. Cl.
CPC ...... *A61B 17/0487* (2013.01); *A61B 17/0469* (2013.01); *A61B 17/0483* (2013.01);
(Continued)

(58) Field of Classification Search
CPC ............ A61B 17/0487; A61B 17/0469; A61B 17/0483; A61B 2017/0496; A61B 2017/00243; A61B 2017/0488
See application file for complete search history.

(56) References Cited

U.S. PATENT DOCUMENTS 5,520,702 A * 5/1996 Sauer ................. A61B 17/0469
606/139
6,152,934 A  11/2000 Harper et al.
(Continued)

FOREIGN PATENT DOCUMENTS

| CN | 2349995 Y | 11/1999 |
| CN | 104688284 B9 | 3/2018 |
| CN | 109199468 A | 1/2019 |

OTHER PUBLICATIONS

Extended European Search Report issued corresponding EP Application No. Ep19815347.0 dated Jun. 14, 2021.
(Continued)

*Primary Examiner* — Jing Rui Ou
(74) *Attorney, Agent, or Firm* — HAUPTMAN HAM, LLP (57) ABSTRACT

An adjustable suture locking apparatus includes a lock pin, an outer tube, a handle, and an adjusting device. The lock pin is used to receive or fix a suture. The outer tube defines a receiving cavity. The lock pin is disposed at a distal end of the receiving cavity. The handle includes a fixing portion coupled to a proximal end of the outer tube. The adjusting device is disposed on the fixing portion. The adjusting
(Continued)

device is coupled to a proximal end of the suture and operable to adjust tensioning or loosening of the suture.

17 Claims, 10 Drawing Sheets

(52) U.S. Cl.
CPC ............... *A61B 2017/00243* (2013.01); *A61B 2017/0488* (2013.01); *A61B 2017/0496* (2013.01)

(56) References Cited

U.S. PATENT DOCUMENTS

| | | |
|---|---|---|
| 2003/0204205 A1 | 10/2003 | Sauer et al. |
| 2004/0111114 A1 | 6/2004 | Shikhman et al. |
| 2005/0049597 A1* | 3/2005 | West, Jr. .......... A61B 17/06061 606/88 |
| 2008/0033460 A1* | 2/2008 | Ziniti ................. A61B 17/0401 606/148 |
| 2010/0049213 A1 | 2/2010 | Serina et al. |
| 2010/0094314 A1 | 4/2010 | Hernlund et al. |
| 2011/0172682 A1 | 7/2011 | Brady et al. |
| 2012/0123447 A1* | 5/2012 | Corrao ................... A61B 17/04 606/144 |
| 2016/0166248 A1 | 6/2016 | Deville et al. |
| 2016/0317144 A1* | 11/2016 | Popovici ............ A61B 17/0469 |
| 2016/0354080 A1* | 12/2016 | Sauer ................. A61B 17/0469 |
| 2018/0199935 A1* | 7/2018 | Sugimoto ........ A61B 17/06066 |

OTHER PUBLICATIONS

International Search Report issued corresponding PCT application No. PCT/CN2019/087885 dated Jul. 12, 2019.

* cited by examiner

ADJUSTABLE SUTURE LOCKING APPARATUS

RELATED APPLICATIONS

The present application is a National Phase of International Application Number PCT/CN/2019/087885, filed on May 22, 2019, which claims priority to Chinese Patent Application No. 201810587805.9, filed on Jun. 8, 2018, and Chinese Patent Application No. 201820892356.4, filed on Jun. 8, 2018.

TECHNICAL FIELD

This disclosure belongs to the field of medical appliances, and particularly relates to an adjustable suture locking apparatus.

BACKGROUND

During surgery, an operation step of knotting and fixing sutures is often required. A traditional surgical operation is performed under direct vision, and the sutures may usually be knotted manually by a doctor. However, with the development of technology, various minimally invasive surgeries and interventional surgeries such as an endoscopic surgery and a transcatheter interventional surgery are increasingly becoming common. For these surgeries, patient's body only needs to be incised to form a relatively small incision that acts as an operating window, and through the operating window instruments such as endoscopes or interventional catheters are pushed into the patient's body until the instruments reach a predetermined position to perform treatment. For these surgeries, if the sutures need to be knotted or fixed, the operator usually needs to perform, through the relatively small operating window, a remote operation outside the patient's body to knot the sutures disposed in the patient's body.

In the related art, methods such as a surgical robot, a thread knot pusher, or a transcatheter suture lock implanting system are often used to perform long-distance knotting or fixing of the sutures. However, when these methods are used to lock the sutures, lengths of the sutures cannot be adjusted according to surgical situations and therapeutic effects.

SUMMARY

In view of the above problems, an adjustable suture locking apparatus is provided according to the present disclosure. The detailed technical solution is as follows.

An adjustable suture locking apparatus is provided. The adjustable suture locking apparatus includes a lock pin, an outer tube, a handle, and an adjusting device. The lock pin is operable to receive or fix a suture. The outer tube defines a receiving cavity. The lock pin is disposed at a distal end of the receiving cavity. The handle includes a fixing portion coupled to a proximal end of the outer tube. The adjusting device is disposed on the fixing portion. The adjusting device is coupled to a proximal end of the suture and operable to adjust tensioning or loosening of the suture.

With regard to the adjustable suture locking apparatus provided in the present disclosure, in a minimally invasive surgery or an interventional surgery, according to efficacy, a length of the suture can be timely adjusted in a process of fixing the suture, thereby enhancing a surgical effect and improving a surgery success rate.

BRIEF DESCRIPTION OF THE ACCOMPANYING DRAWINGS

To illustrate the technical solution in the implementations of the present disclosure more clearly, the following briefly introduces the accompanying drawings required for describing the implementations. Obviously, the accompanying drawings in the following description are merely some implementations of the present disclosure, and based on these accompanying drawings, those of ordinary skill in the art may also derive other accompanying drawings without creative efforts.

FIGS. 7a-7b are schematic structural views illustrating a handle of an adjustable suture locking apparatus according to a second implementation of the present disclosure, wherein

FIG. 15a is a schematic view illustrating that the lock pin is not held and pressed by the adjustable suture locking apparatus, and FIG. 15b is a schematic view illustrating that the lock pin is held and pressed by the adjustable suture locking apparatus, wherein FIG. 15a is an enlarged view of a portion C of FIG. 14b.

DETAILED DESCRIPTION OF ILLUSTRATED IMPLEMENTATIONS

The technical solution in the implementations of the present disclosure will be described clearly and completely hereinafter with reference to the accompanying drawings in the implementations of the present disclosure. Obviously, the described implementations are merely some but not all implementations of the present disclosure. Based on the implementations of the present disclosure, all other implementations obtained by a person of ordinary skill in the art without creative efforts shall fall within the protection scope of the present disclosure.

Orientation definition: an orientation close to an operator is defined as a proximal end, and another orientation away from the operator is defined as a distal end.

Figure 1:
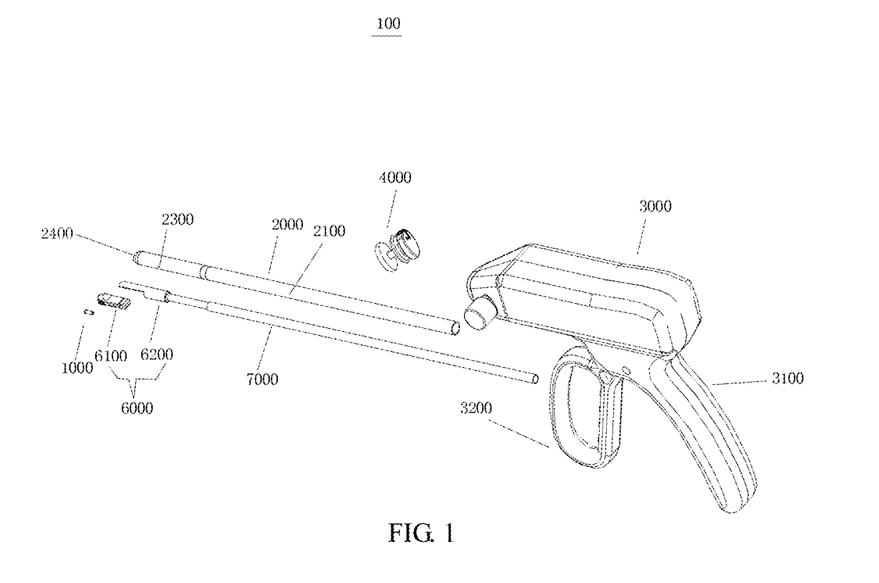
FIG. 1 is a schematic structural view illustrating an adjustable suture locking apparatus according to a first implementation of the present disclosure.
Figure 2A:
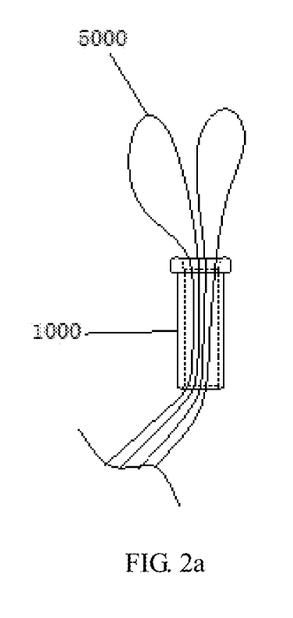
FIG. 2a is a schematic view illustrating that a suture is not fixed by a lock pin according to the present disclosure.
Figure 2B:
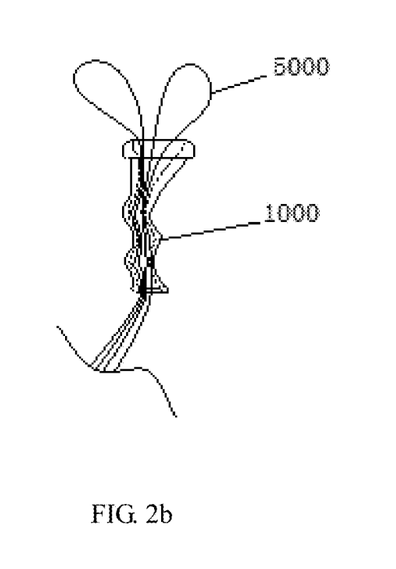
FIG. 2b is a schematic view illustrating that the suture is fixed by the lock pin according to the present disclosure.
Figure 3A:
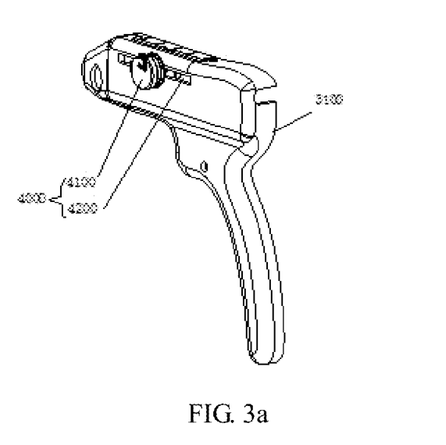
FIGS. 3a-3c are schematic structural views illustrating a handle of the adjustable suture locking apparatus according to a first implementation of the present disclosure.
Figure 3B:
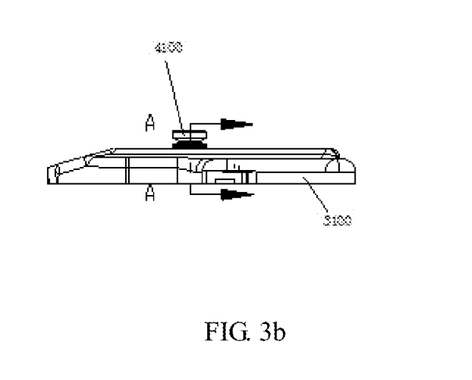
Figure 3C:
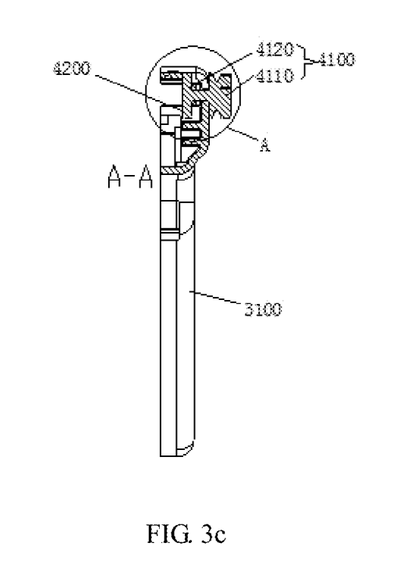
Figure 15A:
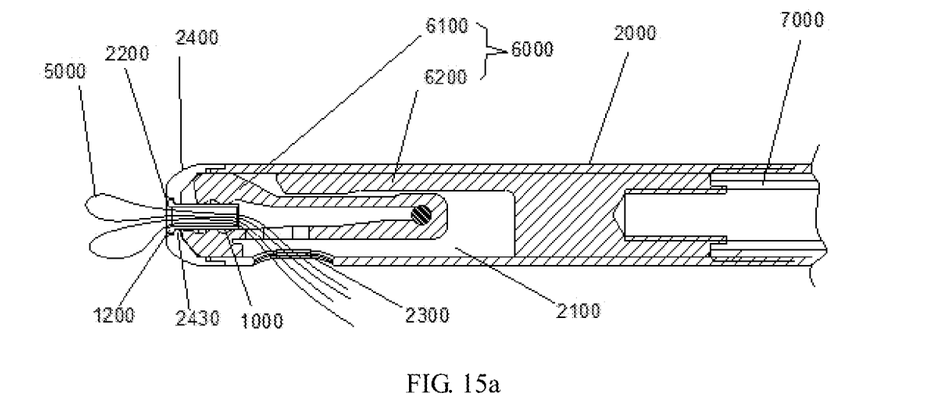

As illustrated in FIG. 1, an adjustable suture locking apparatus 100 is provided according to a first implementation of the present disclosure. The adjustable suture locking apparatus 100 includes a lock pin 1000, an outer tube 2000, a handle 3000, and at least one adjusting device 4000. The lock pin 1000 is used to accommodate or fix the suture 5000 (referring to FIG. 2a or 2b, wherein FIG. 2a illustrates that the suture 5000 is not fixed by the lock pin 1000, and FIG. 2b illustrates that the suture 5000 is fixed by the lock pin 1000). The outer tube 2000 defines a receiving cavity 2100, and the lock pin 1000 is disposed at a distal end of the receiving cavity 2100 (as illustrated in FIG. 15). The handle 3000 includes a fixing portion 3100 coupled to a proximal end of the outer tube 2000. The adjusting device 4000 is disposed on the fixing portion 3100 (as illustrated in FIGS. 3a-3c). The adjusting device 4000 is coupled to the proximal end of the suture 5000 and used for adjusting tightening or loosening of the suture 5000. It can be understood that the adjusting device 4000 may be any device capable of adjusting the tightening or loosening of the suture 5000, such as a bunching device or a buckle. It can be understood that the number of the at least one adjusting device 4000 can be set according to need. Preferably, two adjusting devices 4000 are respectively disposed on two opposite sides of the fixing portion 3100 for adjusting two sets of sutures 5000 respectively.

With regard to the adjustable suture locking apparatus 100 provided by the present disclosure, in a minimally invasive surgery or interventional surgery, the adjusting device 4000 can be used to timely adjust, according to efficacy, the length of the suture 5000 in a process of fixing the suture 5000, thereby enhancing a surgical effect and improving a surgery success rate.

As illustrated in FIGS. 3a-3c, in a further implementation, the adjusting device 4000 includes a bunching device 4100 movably coupled to the fixing portion 3100. The bunching device 4100 is coupled to the proximal end of the suture 5000 to adjust the tightening or loosening of the suture 5000. By adjusting the tightening or loosening of the suture 5000 through the bunching device 4100, the length of the suture 5000 can be effectively controlled, and a slight adjustment of the length of the suture 5000 can be achieved. For example, the suture 5000 is wound on the bunching device 4100, and the suture 5000 is tightened or loosened by changing a winding direction or a winding manner.

In a further implementation, the adjusting device 4000 further includes an adjusting rail 4200 disposed on the fixing portion 3100. The bunching device 4100 is coupled to the fixing portion 3100 via the adjusting rail 4200. The bunching device 4100 can slide back and forth on the adjusting rail 4200 along an axial direction of the adjusting rail 4200, thereby adjusting the tightening or loosening of the suture 5000. It is to be understood that the bunching device 4100 adjusts the tightening or loosening of the suture 5000 when rolling on the adjusting rail 4200. It is to be understood that the axial direction of the adjusting rail 4200 coincides with the axial direction of the whole adjustable suture locking apparatus 100, or the axial direction of the adjusting rail 4200 and the axial direction of the whole adjustable suture locking apparatus 100 define an angle of preset degrees, so as to allow the bunching device 4100 to roll on the adjusting rail 4200, thereby adjusting the tightening or loosening of the suture 5000. The axial direction of the whole adjustable suture locking apparatus 100 refers to a direction from the proximal end to the distal end.

Figure 6:
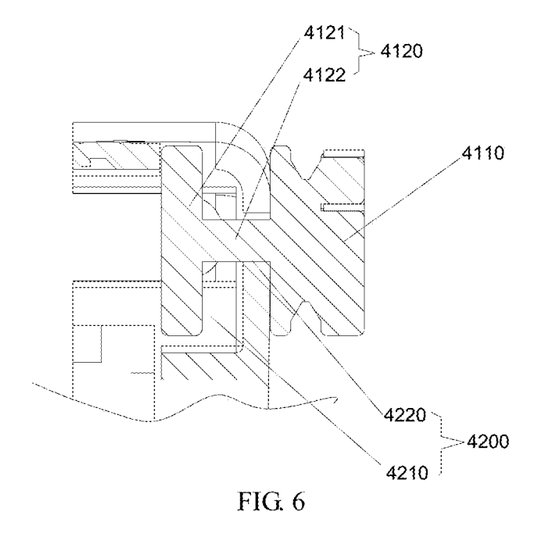
FIG. 6 is an enlarged view of a portion A of FIG. 3c.

As illustrated in FIGS. 4a-4b and FIGS. 3a-3c, in a further implementation, the bunching device 4100 includes a suture fixation 4110 and a handle connecting portion 4120 coupled with the suture fixation 4110. The suture fixation 4110 is detachably coupled to the suture 5000. The suture 5000 can be fixed to the suture fixation 4110 by winding, pressing, fastening, or the like. The handle connecting portion 4120 is disposed in the adjusting rail 4200 (as illustrated in FIG. 6). The bunching device 4100 can move back and forth on the adjusting rail 4200 along the axial direction of the adjusting rail 4200 via the handle connecting portion 4120. The handle connecting portion 4120 is disposed in the adjusting rail 4200 by snapping or the like to ensure that the bunching device 4100 cannot slip off the handle 3000.

Figure 4A:
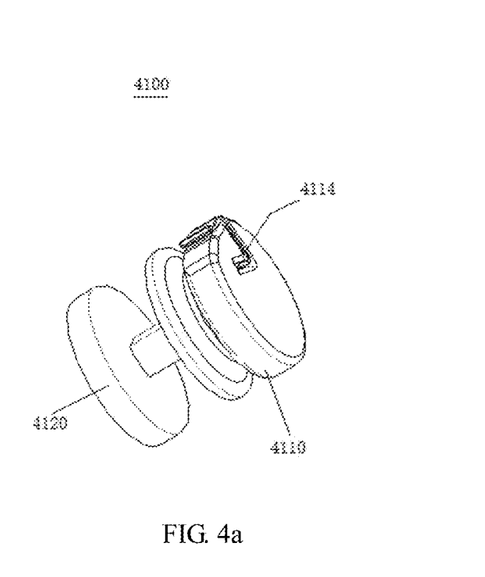
FIGS. 4a-4b are schematic structural views illustrating a bunching device of the adjustable suture locking apparatus according to the first implementation of the present disclosure.
Figure 4B:
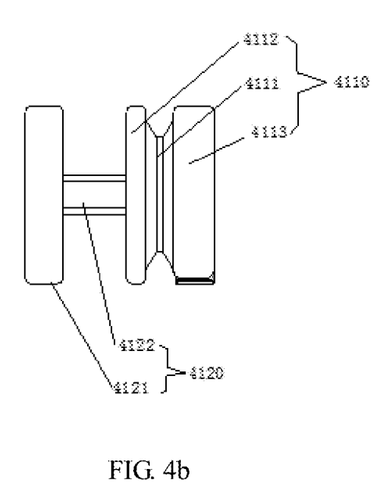

As illustrated in FIG. 4b, in a further implementation, the suture fixation 4110 includes a spool 4111, a first blocking portion 4112, and a second blocking portion 4113. The first blocking portion 4112 and the second blocking portion 4113 are respectively coupled to two opposite ends of the spool 4111. The second blocking portion 4113 is further away from the handle connecting portion 4120 than the first blocking portion 4112. When the suture 5000 is wound on the spool 4111, the first blocking portion 4112 and the second blocking portion 4113 at two ends of the spool 4111 can effectively prevent the suture 5000 from slipping off the spool 4111. It is to be understood that the first blocking portion 4112 and the second blocking portion 4113 each have a larger diameter than the spool 4111.

Figure 5:
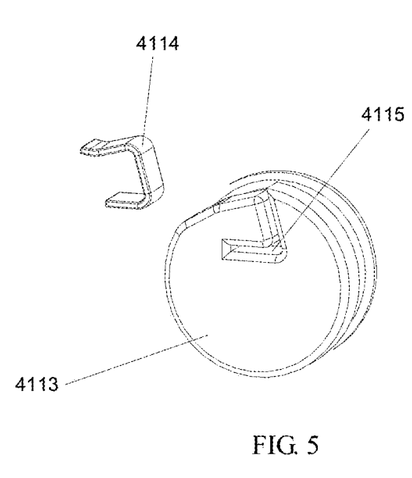
FIG. 5 is a schematic structural view illustrating a suture fixation of the bunching device of the adjustable suture locking apparatus according to the first implementation of the present disclosure.

Referring to FIG. 4a, in a further implementation, the suture fixation 4110 further includes an elastic sheet 4114. The elastic sheet 4114 is fixed to the second blocking portion 4113. The elastic sheet 4114 is used to fix the suture 5000. Referring to FIG. 5, it is to be understood that the second blocking portion 4113 defines an elastic sheet receiving groove 4115. The elastic sheet 4114 is received in the elastic sheet receiving groove 4115. After the suture 5000 is wound on the spool 4111 several times, the proximal end of the suture 5000 is fixed to the elastic sheet 4114 and received in the elastic sheet receiving groove 4115 to fix the proximal end of the suture 5000 to the bunching device 4100. It can be understood that the elastic sheet receiving groove 4115 may be designed to be in a shape of a corner, and the elastic sheet 4114 is designed to be adapted to the elastic sheet receiving groove 4115 having the shape of a corner. With setting of the shape of a corner, the suture 5000 cannot easily slip off the elastic sheet 4114 and is stably fixed.

As illustrated in FIGS. 3a-3c and FIG. 6, FIG. 6 is an enlarged view of a portion A of FIG. 3c. In a further implementation, the adjusting rail 4200 defines a rail cavity 4210 and has a rail outer wall 4220. The handle connecting portion 4120 includes an inserting end 4121 and a connecting shaft 4122. The inserting end 4121 is disposed in the rail cavity 4210 and can move back and forth in the rail cavity 4210. The connecting shaft 4122 is disposed on the rail outer wall 4220 and can move back and forth on the rail outer wall 4220. The inserting end 4121 is fixed to the suture fixation 4110 via the connecting shaft 4122. The inserting end 4121 is disposed in the rail cavity 4210, and movement of the inserting end 4121 is limited to be within the rail cavity 4210 due to the rail outer wall 4220, and thus the inserting end 4121 cannot easily slip off the rail cavity 4210.

Figure 7A:
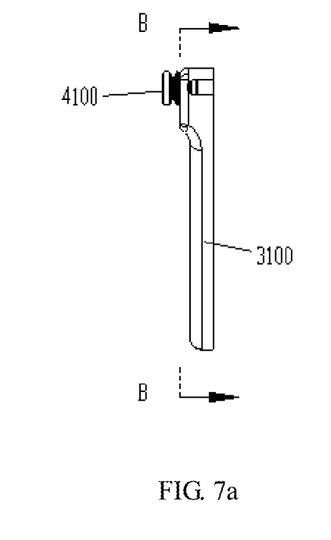
Figure 7B:
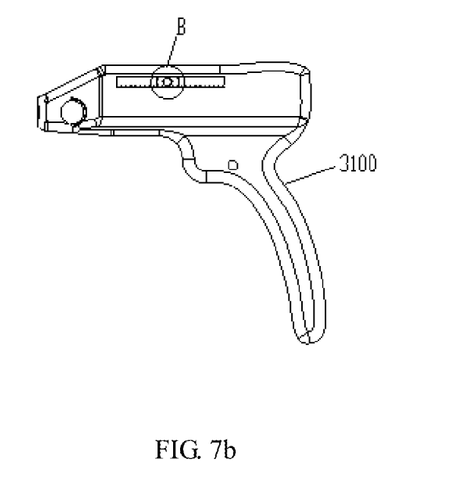
FIG. 7b is a cross-sectional view of the handle illustrated in FIG. 7a, taken along line B-B.
Figure 8:
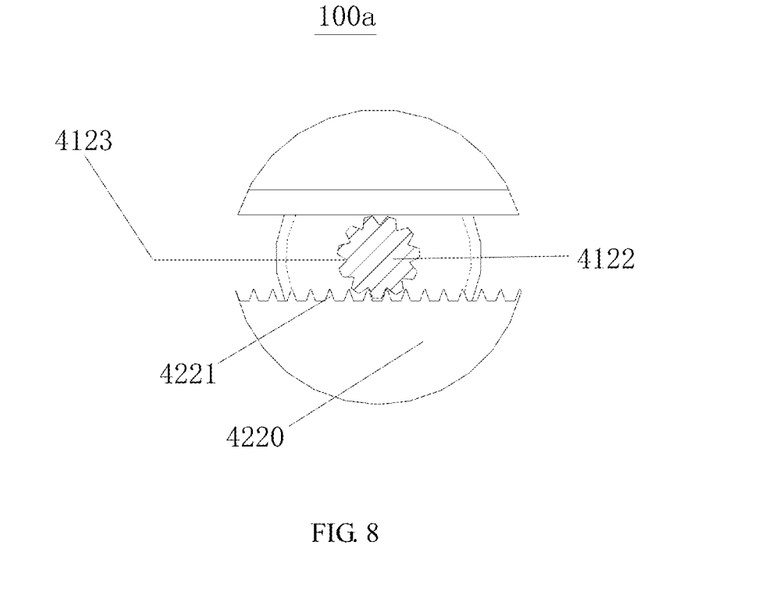
FIG. 8 is an enlarged view of a portion B of FIG. 7b.

As illustrated in FIGS. 7a-7b and FIG. 8, an adjustable suture locking apparatus 100a according to a second implementation of the present disclosure is illustrated. FIG. 7a is a right view of the adjustable suture locking apparatus 100a, where a handle of the suture locking apparatus 100a is viewed. FIG. 7b is a cross-sectional view of the adjustable suture locking apparatus 100a illustrated in FIG. 7a, taken along line B-B. FIG. 8 is an enlarged view of a portion B of FIG. 7b. The adjustable suture locking apparatus 100a differs from the adjustable suture locking apparatus 100 in the first implementation in that the adjustable suture locking apparatus 100a is provided with first teeth 4221 on the rail outer wall 4220 and second teeth 4123 on the connecting shaft 4122. The first teeth 4221 can be engaged with the second teeth 4123 to enable the connecting shaft 4122 to roll on the rail outer wall 4220, thereby driving the bunching device 4100 to move back and forth on the adjusting rail 4200 along the axial direction of the adjusting rail 4200. When the operator rotates the bunching device 4100, the bunching device 4100 moves along the axial direction of the adjusting rail 4200, and a rotational motion of the bunching device 4100 can be converted into a linear motion of the suture 5000, thereby accurately achieving the tightening and loosening of the suture 5000.

Figure 9:
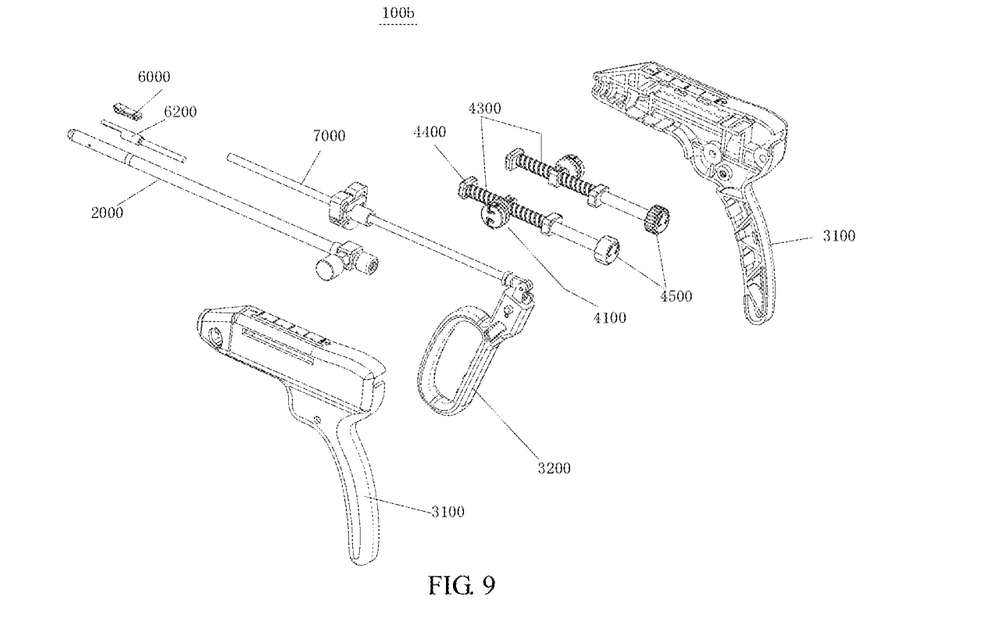
FIG. 9 is a schematic structural view illustrating an adjustable suture locking apparatus according to a third implementation of the present disclosure.
Figure 10:
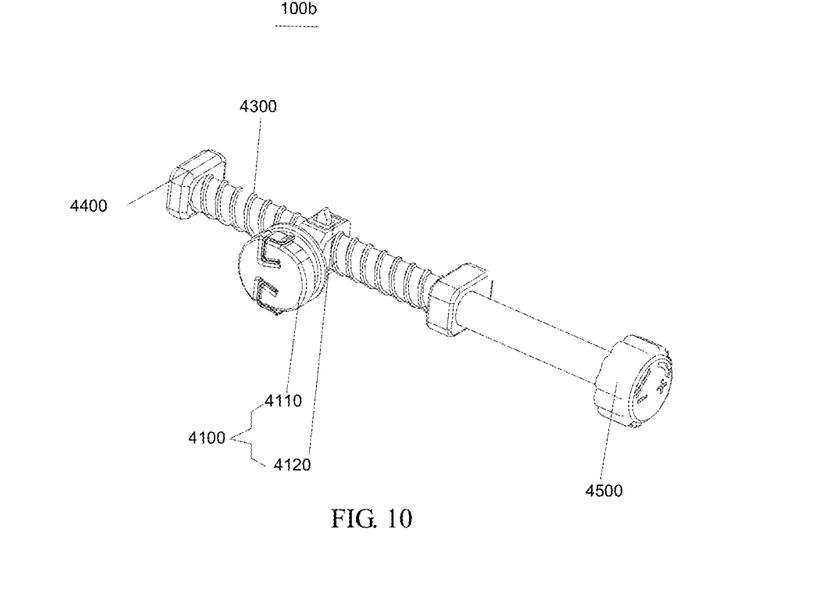
FIG. 10 is a schematic structural view illustrating an adjusting device of the adjustable suture locking apparatus according to the third implementation of the present disclosure.

As illustrated in FIGS. 9-10, an adjustable suture locking apparatus 100b according to a third implementation is illustrated. The adjustable suture locking apparatus 100b differs from the adjustable suture locking apparatus 100 in the first implementation in that the adjusting device 4000 further includes a lead screw 4300, a bolt 4400, and an adjusting knob 4500. The lead screw 4300 is fixed in the fixing portion 3100 along the axial direction of the adjusting rail 4200. The bolt 4400 is fixed in the fixing portion 3100, and the lead screw 4300 passes through the bolt 4400 and is engaged with the bolt 4400. A proximal end of the lead screw 4300 passes through the proximal end of the fixing portion 3100 and is coupled to the adjusting knob 4500. The handle connecting portion 4120 is fixed to the lead screw 4300. The adjusting knob 4500 can adjust an axially forward or backward movement of the lead screw 4300. When the operator rotates the adjusting knob 4500, the adjusting knob 4500 drives the lead screw 4300 to rotate in the fixing portion 3100, thereby driving the bunching device 4100 coupled to the lead screw 4300 to move back and forth on the adjusting rail 4200 along the axial direction of the adjusting rail 4200.

Figure 11:
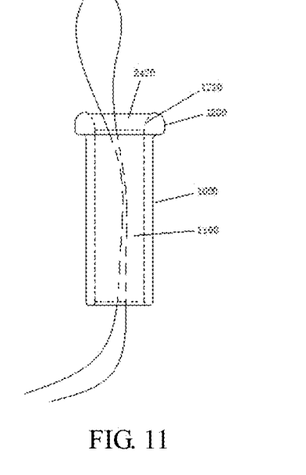
FIG. 11 is a perspective view illustrating the lock pin according to the present disclosure.

Referring back to FIG. 1, in a further implementation, the handle 3000 further includes a movable portion 3200. The movable portion 3200 can move with respect to the fixing portion 3100. The lock pin 1000 defines a hollow inner cavity 1100 in the axial direction of the lock pin 1000 (as illustrated in FIG. 11). The hollow inner cavity 1100 is used to receive the suture 5000 and allow the suture 5000 to pass through. The adjustable suture locking apparatus 100 further includes a squeezing assembly 6000 and a mandrel 7000. The squeezing assembly 6000 is used to hold and press the lock pin 1000 to deform the lock pin 1000 (referring to FIGS. 2a-2b, wherein FIG. 2a illustrates the lock pin undeformed, and FIG. 2b illustrates the lock pin deformed). When the lock pin 1000 is subjected to a mechanical external force, the lock pin 1000 can be flattened to fix the suture 5000 in the lock pin 1000, and no relative movement occurs between the suture 5000 and the lock pin 1000, thereby locking and fixing the suture 5000. The lock pin 1000 may be of various shapes, for example, may be in the shape of a cylinder, a prism, or the like. As long as the lock pin 1000 defines the hollow inner cavity 1100 for accommodating the suture 5000, the lock pin 1000 may be of any shape. In this implementation, the lock pin 1000 is in the shape of a cylinder to reduce a squeezing resistance.

Figure 14A:
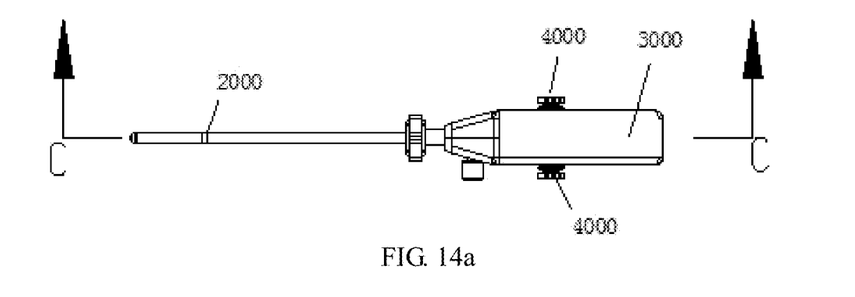
FIGS. 14a-14b are schematic views illustrating holding and pressing the lock pin by the adjustable suture locking apparatus according to the present disclosure.
Figure 14B:
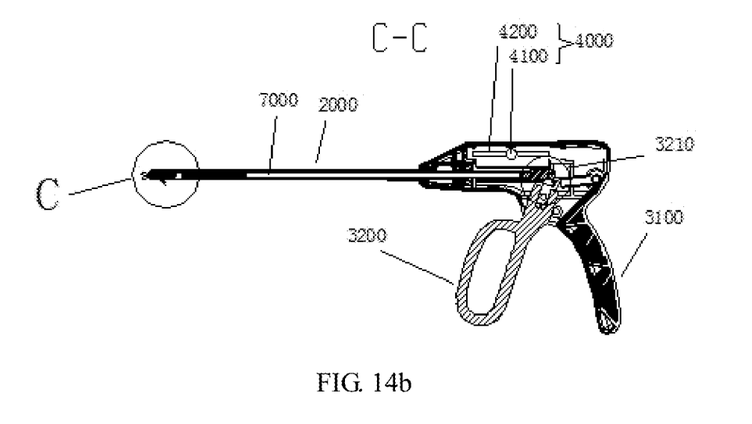

A distal end of the mandrel 7000 is coupled to a proximal end of the squeezing assembly 6000, and a proximal end of the mandrel 7000 is movably coupled to the movable portion 3200. The squeezing assembly 6000 and the mandrel 7000 are both received in the receiving cavity 2100, and the movable portion 3200 can move relative to the fixing portion 3100 to move the mandrel 7000, so as to cause the squeezing assembly 6000 to hold and press the lock pin 1000. It can be understood that the mandrel 7000 applies a force to the squeezing assembly 6000 during the movement of the mandrel 7000, so that the squeezing assembly 6000 can apply a mechanical external force to hold and press the lock pin 1000. The mandrel 7000 can extend to the fixing portion 3100, and a movable connecting portion 3210 between the movable portion 3200 and the mandrel 7000 is disposed in the fixing portion 3100 (as illustrated in FIGS. 14a-14b).

Figure 12:
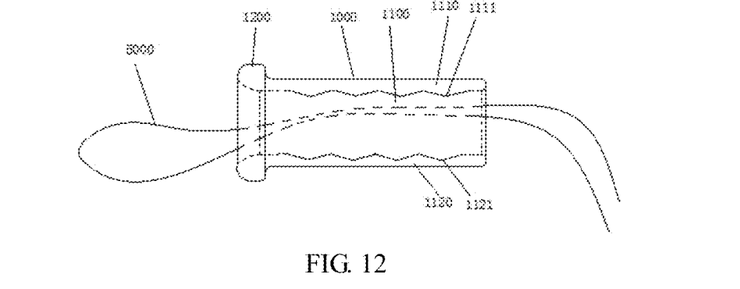
FIG. 12 is a perspective view illustrating a lock pin according to another implementation of the present disclosure.

As illustrated in FIG. 12, in a further implementation, the hollow inner cavity 1100 of the lock pin 1000 has an upper surface 1110 and a lower surface 1120 opposite the upper surface 1110. A lock pad 1111 protrudes from the upper surface 1110, the lower surface 1120 defines a concave lock hole 1121, and the lock pad 1111 is adapted to the lock hole 1121. It can be understood that the upper surface and the lower surface are named when the lock pin 1000 is placed horizontally, and when the lock pin 1000 is placed vertically, the upper surface and the lower surface may also be called a left surface and a right surface. When the lock pin 1000 is deformed by an external squeezing force, the convex lock pad 1111 is pressed into the concave lock hole 1121. When the lock pin 1000 is further deformed, the lock pad 1111 and the lock hole 1121 are both deformed until the lock pad 1111 and the lock hole 1121 cannot be separated from each other. At this point, the suture 5000 is firmly fixed in the hollow inner cavity 1100 of the lock pin 1000.

Figure 13:
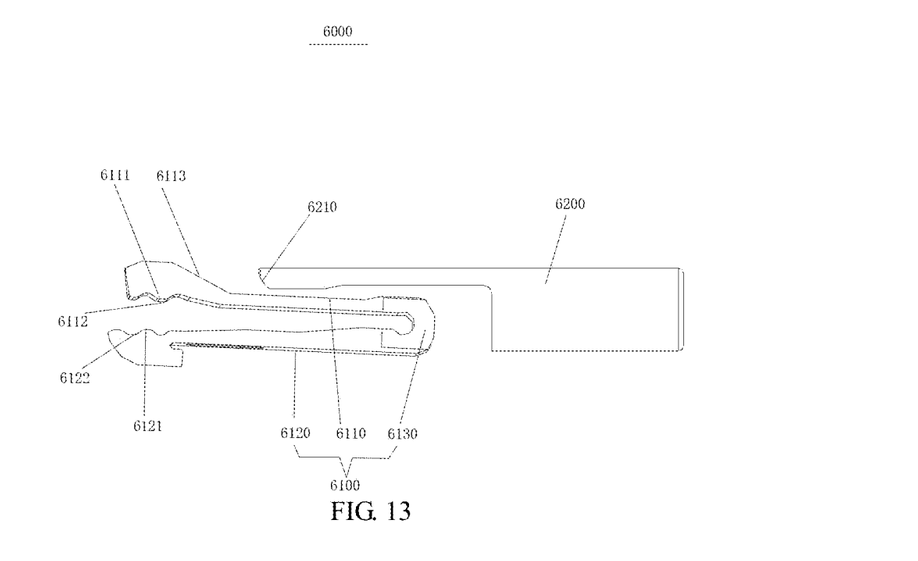
FIG. 13 is a schematic structural view illustrating a squeezing assembly according to the present disclosure.
Figure 15B:
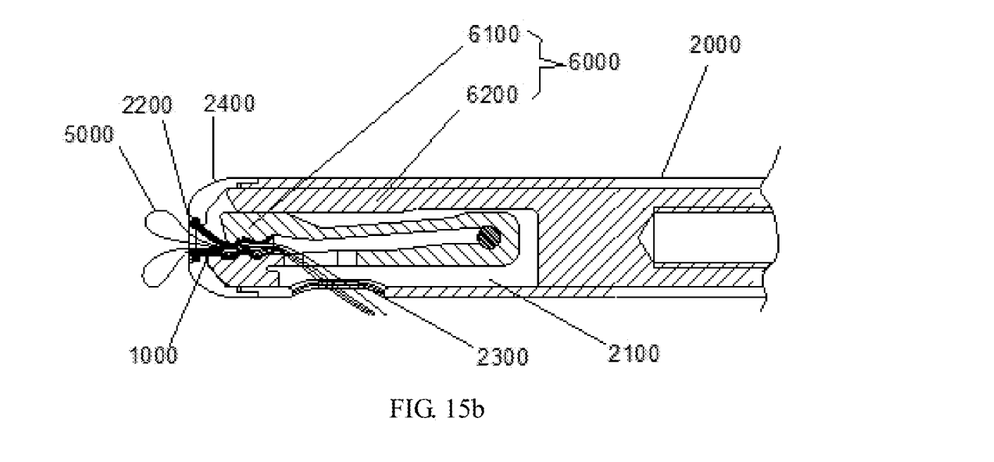

As illustrated in FIG. 13 and FIGS. 15a-15b, in a further implementation, the squeezing assembly 6000 includes a collet 6100 and a pushing rod 6200. The collet 6100 includes an upper clip 6110, a lower clip 6120, and a clip connecting portion 6130 coupled between a proximal end of the upper clip 6110 and a proximal end of the lower clip 6120. The lock pin 1000 is disposed between the upper clip 6110 and the lower clip 6120. A proximal end of the pushing rod 6200 is coupled to the distal end of the mandrel 7000. A distal end of the pushing rod 6200 is close to the upper clip 6110. The mandrel 7000 drives the pushing rod 6200 to move toward the upper clip 6110, thereby driving the upper clip 6110 to move toward the lower clip 6120 to make the upper clip 6110 and the lower clip 6120 cooperatively hold and press the lock pin 1000.

It is to be understood that, the upper clip 6110 and/or the lower clip 6120 are/is at least partially made from a deformable material and have/has certain elasticity. Therefore, when the upper clip 6110 and/or the lower clip 6120 are/is subjected to an external force, the deformable upper clip 6110 and/or the deformable lower clip 6120 may be driven to be close to each other, so as to hold and press the lock pin 1000 disposed between the upper clip 6110 and the lower clip 6120 to form a shape with a certain curvature. It can be understood that the upper clip 6110 and the lower clip 6120 are preferably made of stainless steel, nickel titanium alloy, cobalt chromium alloy or the like, and the clip connecting portion 6130 is made of stainless steel, nickel titanium alloy or the like. In this implementation, the whole collet 6100 is made of nickel-titanium alloy.

Still referring to FIG. 13, in a further implementation, the upper clip 6110 has a first surface 6111 that faces the lock pin 1000, and the lower clip 6120 has a second surface 6121 that faces the lock pin 1000. A first engaging portion 6112 is formed on the first surface 6111, a second engaging portion 6122 is formed on the second surface 6121, and the first engaging portion 6112 can be engaged with the second engaging portion 6122 to enable the upper clip 6110 and the lower clip 6120 to be in a close state. It can be understood that the first engaging portion 6112 and the second engaging portion 6122 each may have a curvature shape or a sawtooth shape and can cooperate with each other.

When the lock pin 1000 is provided with a circular cone 1200 at the distal end thereof (see FIG. 12), the diameter of the circular cone 1200 is larger than that of the proximal end of the lock pin 1000. In order to cooperate with the lock pin 1000 with the circular cone 1200, in a further implementation, axial lengths of the upper clip 6110 and the lower clip 6120 are different from each other. Preferably, a difference between the axial length of the upper clip 6110 and the axial length of the lower clip 6120 equals a preset length. The preset length is at least equal to the thickness of the circular cone 1200. Thus, the circular cone 1200 of the lock pin 1000 non-pressed and the collet 6100 can be both placed at the distal end of the outer tube 2000 without affecting a size of the outer tube 2000. The thickness of the circular cone 1200 refers to the length of the circular cone 1200 along the axial direction of the lock pin 1000.

In a further implementation, the distal end of the pushing rod 6200 has a first inclined surface 6210, and the first inclined surface 6210 is inclined downwardly along a direction from the distal end to the proximal end. The upper clip 6110 has a second inclined surface 6113 that faces away from the lock pin 1000, and the second inclined surface 6113 is inclined downwardly along a direction from the distal end to the proximal end to ensure that there is a relatively large contact area between the collet 6100 and the pushing rod 6200. Preferably, a slope of the first inclined surface 6210 is smaller than that of the second inclined surface 6113. The slope of the first inclined surface 6210 refers to an included angle defined between the first inclined surface 6210 and a direction from the distal end of the pushing rod 6200 to the proximal end of the pushing rod 6200, and the slope of the second inclined surface 6113 refers to an included angle defined between the second inclined surface 6113 and a direction from the distal end of the pushing rod 6200 to the proximal end of the pushing rod 6200, and thus during that the pushing rod 6200 is moved toward the distal end, the first inclined surface 6210 at the distal end of the pushing rod 6200 can continuously squeeze the second inclined surface 6113 of the upper clip 6110, so that the upper clip 6110 gradually gets close to the lower clip 6120, thereby continuously deforming the lock pin 1000 until the lock pin 1000 can no longer be deformed. At this point, the lock pin 1000 and the suture 5000 are firmly fixed together. The pushing rod 6200 is made of stainless steel, nickel-titanium alloy, or cobalt-chromium alloy, and is preferably made of stainless steel.

It can be understood that the distal end of the pushing rod 6200 and the proximal end of the pushing rod 6200 form an L-shaped structure, that is, a radial thickness of the distal end of the pushing rod 6200 is smaller than that of the proximal end of the pushing rod 6200, and the distal end of the pushing rod 6200 is at one side of the whole pushing rod 6200, such that the distal end of the pushing rod 6200 and the proximal end of the pushing rod 6200 form the L-shaped structure. When the pushing rod 6200 is advanced to hold and press the collet 6100 downwardly, the L-shaped pushing rod 6200 enables the collet 6100 in the pressed state to be disposed in the L-shaped structure, such that a difference between a thickness of the whole structure formed by the pushing rod 6200 when the collet 6100 is pressed and a thickness of the collet 6100 non-pressed is relatively small, thereby not affecting the size of the outer tube 2000.

It can be understood that the pushing rod 6200 may be a hollow tube or have a solid rod-like structure.

Referring to FIGS. 14*a*-14*b*, FIG. 15*a*, FIG. 15*b*, FIG. 15*a* is a schematic view illustrating that the lock pin is not held and pressed by the adjustable suture locking apparatus, and FIG. 15*b* is a schematic view illustrating that the lock pin is held and pressed by the adjustable suture locking apparatus, wherein FIG. 15*a* is an enlarged view of a portion C of FIG. 14*b*. In a further implementation, the distal end of the outer tube 2000 defines a suture inlet 2200 along the radial direction of the outer tube 2000. A diameter of the suture inlet 2200 is at least equal to the diameter of a portion of the lock pin 1000, where the portion of the lock pin 1000 has a maximum outer diameter, and thus the lock pin 1000 pressed can slip off the distal end of the outer tube 2000. The outer tube 2000 further defines a suture outlet 2300. The suture inlet 2200 and the suture outlet 2300 communicate with the hollow inner cavity 1100 of the lock pin 1000, respectively, so that the proximal end of the suture 5000 can sequentially pass through the suture inlet 2200, the proximal end of the lock pin 1000, and the suture outlet 2300. It can be understood that, in other implementations, the suture outlet 2300 may be in any position of the outer tube 2000 or in the handle 3000, as long as the suture outlet 2300 communicates with the hollow inner cavity 1100 of the lock pin 1000, i.e., the proximal end of the suture 5000 can pass through the suture outlet 2300.

In a further implementation, the outer tube 2000 is provided with a holding portion 2400 at the distal end thereof, and the diameter of the holding portion 2400 gradually decreases from the proximal end to the distal end. The holding portion 2400 is used to prevent the lock pin 1000 non-pressed from slipping off the distal end of the outer tube 2000. The diameter of the holding portion 2400 gradually reduces from the proximal end to the distal end, thereby facilitating driving the distal end of the outer tube 2000 to enter the patient's body and smoothly move in the body.

Figure 16A:
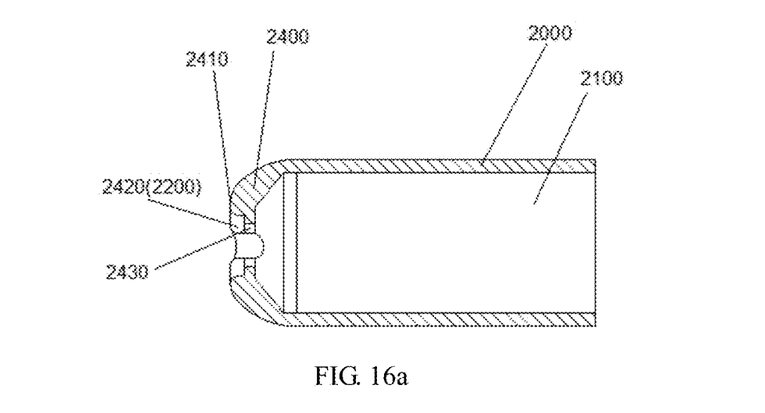
FIGS. 16a-16b are schematic structural views illustrating a holding portion of the adjustable suture locking apparatus according to the present disclosure.
Figure 16B:
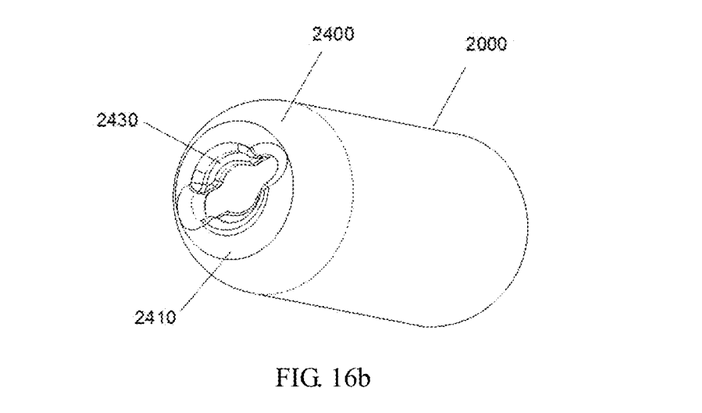

As illustrated in FIGS. 16*a* and 16*b*, in a further implementation, the holding portion 2400 has a holding portion end surface 2410 at the distal end thereof. The holding portion 2400 defines an opening 2420 in the axial direction of the holding portion 2400, and the opening 2420 extends through the holding portion end surface 2410 and communicates with the receiving cavity 2100. The opening 2420 is the suture inlet 2200.

In a further implementation, a protrusion 2430 is formed at the opening 2420 in a radial direction of the opening 2420 (see FIG. 15*a*). A preset distance exists between the protrusion 2430 and the holding portion end surface 2410. The lock pin 1000 is partially disposed in the opening 2420, so that the protrusion 2430 can fix the lock pin 1000.

As illustrated in FIG. 16*a*, FIG. 16*b*, FIG. 15*a*, FIG. 15*b*, and FIG. 11, in a further implementation, the lock pin 1000 is provided with the circular cone 1200 at the distal end thereof. The diameter of the circular cone 1200 is larger than that of the proximal end of the lock pin 1000, and the circular cone 1200 is disposed in the opening 2420. The protrusion 2430 fixes the lock pin 1000, thereby preventing the lock pin 1000 from slipping off the distal end of the outer tube 2000. With the circular cone 1200, the transition between the hollow inner cavity 1100 of the lock pin 1000 and the distal end of the lock pin 1000 is enabled to be smooth to the greatest extent, thereby preventing a connection portion between the hollow inner cavity 1100 and the distal end of the lock pin 1000 from cutting off the suture 5000 or scratching internal tissues of the patient's body. It can be understood that the preset distance is at least equal to the thickness of the circular cone 1200, so that the circular cone 1200 is arranged between the protrusion 2430 and the holding portion end surface 2410, thereby facilitating stability of the lock pin 1000.

As illustrated in FIG. 11, in a further implementation, the circular cone 1200 has an inner sidewall 1210 that is an arc-shaped surface, such that the suture 5000 can smoothly pass through the lock pin 1000, thereby preventing the lock pin 1000 from cutting off the suture 5000 or damaging human tissues.

In a further implementation, the outer tube 2000 and the mandrel 7000 may both be manufactured by processing a metal material such as stainless steel, nickel titanium, pure titanium or the like, or can be manufactured by processing a polymer material such as acrylonitrile butadiene styrene (ABS), polystyrene (PS), polyether ether ketone (PEEK), or the like. The outer tube 2000 and the mandrel 7000 may be made from the same material or different materials. The outer tube 2000 and the mandrel 7000 may be preferably made of stainless steel.

In a further implementation, the lock pin 1000 is made of stainless steel, pure titanium, nickel titanium, cobalt chromium alloy, or the like, and preferably made of pure titanium or stainless steel.

When using the adjustable suture locking apparatus 100 provided in the first implementation, the operator first enables the proximal end of the suture 5000 to sequentially pass through the suture inlet 2200 on the distal end of the outer tube 2000, the opening on the distal end of the lock pin 1000, and the suture outlet 2300 on the distal end of the outer tube 2000, and then enables the suture 5000 to be fixed to the suture fixation 4110 of the bunching device 4100. The length of the suture 5000 is then adjusted by the adjusting device 4000 according to need. After adjustment, the movable portion 3200 of the handle 3000 is driven to move toward the fixing portion 3100, so as to drive the mandrel 7000 to move toward the distal end with respect to the outer tube 2000, thereby causing the pushing rod 6200 to hold and press the collet 6100. The upper clip 6110 and the lower clip 6120 of the collet 6100 hold and press the lock pin 1000 to deform the lock pin 1000 (Refer to FIG. 15*a* and FIG. 15*b*, wherein FIG. 15*a* illustrates the lock pin 1000 non-pressed, and FIG. 15*b* illustrates the lock pin 1000 pressed), and then the suture 5000 received in the lock pin 1000 is fixed to the lock pin 1000.

When the adjustable suture locking apparatus 100 in the present disclosure is used for repairing the leaflets of the mitral valve, before the lock pin 1000 is held and pressed to fix the suture 5000, the operator can adjust a gap between the anterior leaflet and the posterior leaflet of the mitral valve. Meanwhile, the mitral regurgitation is observed through a medical imaging device. When the mitral regurgitation becomes slightest, the suture 5000 is fixed, thereby realizing a function of adjusting the mitral regurgitation.

The following will illustrate an operation process of the adjustable suture locking apparatus in the present disclosure by taking the mitral valve that has lesions as an example.

The mitral valve is a one-way "valve" between a left atrium (LA for short) and a left ventricle (LV for short) and can ensure blood flow from the left atrium to the left ventricle. The mitral valve in a health state has chordae tendineae. The mitral valve includes two leaflets, i.e., an anterior leaflet and a posterior leaflet. When the left ventricle is in a diastolic state, the anterior leaflet and the posterior leaflet are in an open state, and the blood flows from the left atrium to the left ventricle. When the left ventricle is in a contracted state, the chordae tendineae are stretched to prevent the leaflets from being washed by the blood flow to the left atrium, and the anterior leaflet and the posterior leaflet are in a good close state to ensure blood flow from the left ventricle to an aorta through an aortic valve (AV for short). Different from the mitral valve in the health state, under the condition that the mitral valve has lesions, the mitral valve cannot return to the close state when the left ventricle is in the contracted state, and the momentum of the blood flow can further cause the leaflet to fall into the left atrium, thereby resulting in blood regurgitation. A usage process of the adjustable suture locking apparatus 100*b* provided by the third implementation of the present disclosure is as follows.

Figure 17:
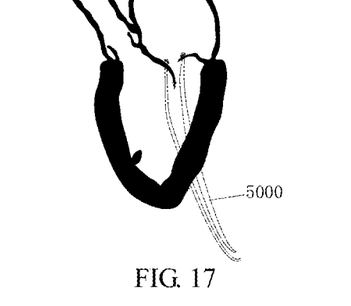
FIG. 17 is a schematic view illustrating implanting sutures into an anterior leaflet and a posterior leaflet according to the present disclosure.

At the first step, multiple sutures 5000 with elastic pads are first implanted into both the anterior leaflet and the posterior leaflet of the mitral valve (see FIG. 17). A point contact between the suture 5000 and the leaflet is changed to a surface contact between the elastic pad and the leaflet, thereby effectively reducing a risk of tearing the leaflet.

Figure 18:
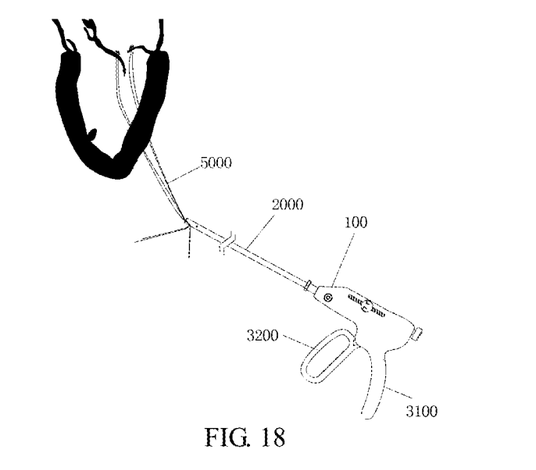
FIG. 18 is a schematic view illustrating that the sutures pass through the adjustable suture locking apparatus according to the present disclosure.

At the second step, outside the patient's body, the multiple sutures 5000 in both the leaflets are all inserted into the lock pin 1000 of the adjustable suture locking apparatus 100*b*, and the proximal ends of the sutures 5000 are enabled to pass through the suture outlet 2300 on the distal body of the outer tube 2000 (see FIG. 18). The sutures in the anterior leaflet and posterior leaflet are distinguished, and the proximal ends of the two sets of sutures 5000 are respectively wound on the spools of the bunching devices 4100 several times, and then the proximal ends of the sutures 5000 are fixed to the elastic sheets 4114 to maintain the relative position between the sutures 5000 and the lock pin 1000 (see FIG. 19). It is to be understood that, at this step, after the sutures 5000 pass through the suture outlet 2300, the distal end of the adjustable suture locking apparatus 100*b* can be first pushed into the heart through the apex of the heart and is moved to be close to the leaflet of the mitral valve, and then the sutures 5000 are fixed to the elastic sheet 4114 respectively (see FIG. 20).

Figure 19:
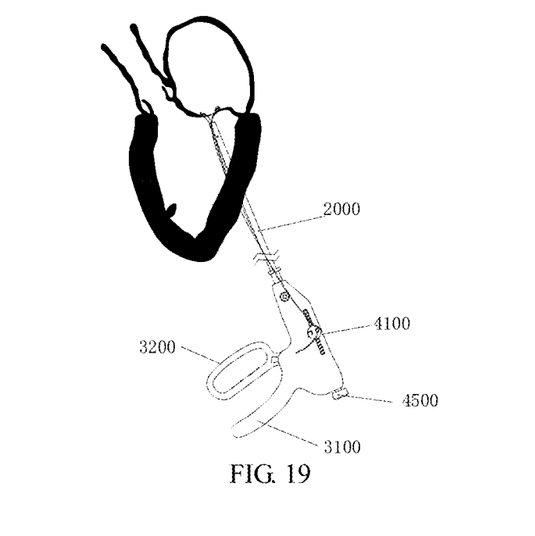
FIG. 19 is a schematic view illustrating that the adjustable suture locking apparatus is operated to adjust lengths of the sutures and hold and press the lock pin according to the present disclosure.
Figure 20:
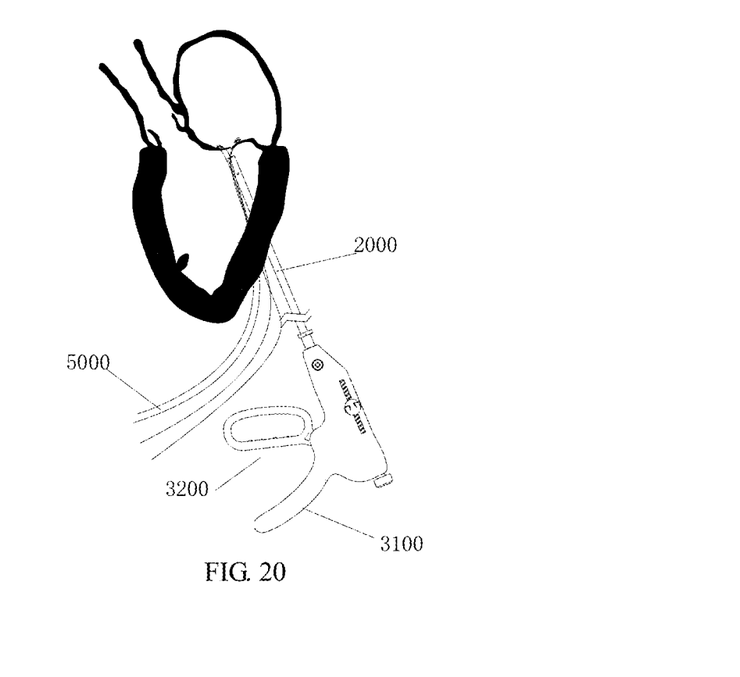
FIG. 20 is a schematic view illustrating pushing the adjustable suture locking apparatus to get close to the leaflets according to the present disclosure.

At the third step, the distal end of the adjustable suture locking apparatus 100b is pushed into the heart through the apex of the heart and is moved to be close to the leaflet of the mitral valve, meanwhile, the sutures 5000 are pulled, until the distal end of the adjustable suture locking apparatus 100b reaches a predetermined position that is below the leaflet (see FIG. 19).

At the forth step, the two adjusting knobs 4500 are rotated respectively to drive the two lead screws 4300 to rotate, thereby driving each bunching device 4100 connected to one lead screw 4300 to move back and forth on the adjusting rail 4200 along the axis direction of the adjusting rail 4200, so as to adjust the tightness of the two sets of sutures 5000 coupled to the bunching devices 4100 respectively, and determine, by ultrasound, a state in which the mitral regurgitation is slightest. When the state reaches, the rotation of the adjusting knobs 4500 are stopped to maintain the tightness of the two sets of sutures 5000, that is, to maintain a relative distance between the anterior leaflet and the posterior leaflet.

At the fifth step, as illustrated in FIG. 14a, FIG. 14b, FIG. 15a, FIG. 15b, and FIG. 19, the fixing portion 3100 of the handle 3000 remains unchanged, and the movable portion 3200 is driven to move toward the fixing portion 3100 until the movable portion 3200 cannot be further moved. At this point, the mandrel 7000 and the pushing rod 6200 move toward the distal end with respect to the outer tube 2000. The distal end of the pushing rod 6200 continuously squeezes the collet 6100, so that the upper clip 6110 and the lower clip 6120 of the collet 6100 get close to each other to hold and press the lock pin 1000 between the upper clip 6110 and the lower clip 6120, until the lock pin 1000 is deformed and the sutures 5000 in the lock pin 1000 are fixed together. The deformed lock pin 1000 slips off the suture inlet 2200 on the distal end of the outer tube 2000 of the adjustable suture locking apparatus 100b.

Figure 21:
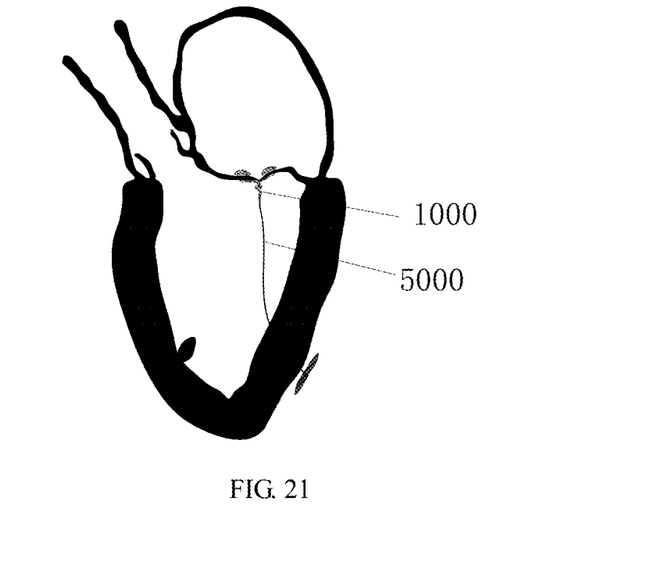
FIG. 21 is a schematic view illustrating that proximal ends of the sutures are fixed to a ventricular wall through the lock pin according to the present disclosure.

At the sixth step, the distal end of the adjustable suture locking apparatus 100b is pulled out of the patient's body, the lock pin 1000 stays in the patient's body, and the proximal end of the sutures 5000 is fixed to the apex of the heart or the papillary muscle. At this point, with the lock pin 1000, the two sets of sutures 5000 in the anterior leaflet and the posterior leaflet are fixed together (see FIG. 21), and edge-to-edge repair for the anterior leaflet and the posterior leaflet of the mitral valve is completed, thereby forming a dual-bore structure. It can be understood that, at this step, the operator does not need to fix the proximal end of the suture 5000 to the apex of the heart or the papillary muscle, and what is needed is to snip the proximal end of the sutures 5000.

The implementations of the present disclosure are described in detail above, and specific examples are used to explain the principles and implementations of the present disclosure. The illustration of the above implementations is only used to help in understanding the method and the core idea of the present disclosure. Also, according to the ideas of the present disclosure, those of ordinary skill in the art can make changes for specific implementations and application scopes. In summary, the content of this specification should not be construed as limiting the present disclosure.

What is claimed is:

1. An adjustable suture locking apparatus comprising:
   a lock pin operable to receive or fix a suture;
   an outer tube defining a receiving cavity, wherein the lock pin is disposed at a distal end of the receiving cavity;
   a handle comprising a fixing portion, wherein the fixing portion is coupled to a proximal end of the outer tube; and
   an adjusting device disposed on the fixing portion, wherein the adjusting device is detachably coupled to a proximal end of the suture and operable to adjust tensioning or loosening of the suture, wherein
   the adjusting device comprises a bunching device movably coupled to the fixing portion and coupled to the proximal end of the suture,
   the bunching device comprises a suture fixation detachably coupled to the suture,
   the suture fixation comprises a spool, a first blocking portion, a second blocking portion, and an elastic sheet,
   the suture is wound around the spool,
   the first blocking portion and the second blocking portion are coupled to two ends of the spool, respectively,
   the second blocking portion is further away from the fixing portion than the first blocking portion, and
   the elastic sheet is fixed to the second blocking portion and operable to fix the suture.

2. The adjustable suture locking apparatus of claim 1, wherein the adjusting device further comprises an adjusting rail, wherein the adjusting rail is disposed on the fixing portion, the bunching device is coupled to the fixing portion via the adjusting rail, and the bunching device is able to move back and forth on the adjusting rail along an axial direction of the adjusting rail to adjust tensioning or loosening of the suture.

3. The adjustable suture locking apparatus of claim 2, wherein the bunching device further comprises a handle connecting portion coupled to the suture fixation, wherein the handle connecting portion is disposed in the adjusting rail, and the bunching device is able to move back and forth on the adjusting rail along the axial direction of the adjusting rail via the handle connecting portion.

4. The adjustable suture locking apparatus of claim 3, wherein
   the adjusting rail comprises a rail cavity and a rail outer wall; and
   the handle connecting portion comprises an inserting end and a connecting shaft, wherein the inserting end is disposed in the rail cavity and able to move back and forth in the rail cavity, the connecting shaft is disposed on the rail outer wall and able to move back and forth on the rail outer wall, and the inserting end is coupled to the suture fixation via the connecting shaft.

5. The adjustable suture locking apparatus of claim 4, wherein the rail outer wall is provided with first teeth, and the connecting shaft is provided with second teeth, wherein the first teeth are able to be engaged with the second teeth to enable the connecting shaft to roll on the rail outer wall.

6. The adjustable suture locking apparatus of claim 3, wherein the adjusting device further comprises a lead screw, a bolt, and an adjusting knob, wherein the lead screw is fixed in the fixing portion along the axial direction of the adjusting rail, the bolt is fixed in the fixing portion, the lead screw passes through the bolt and is engaged with the bolt, a proximal end of the lead screw passes through a proximal end of the fixing portion and is coupled to the adjusting knob, the handle connecting portion is fixed to the lead screw, and the adjusting knob is able to adjust an axially forward or backward movement of the lead screw.

7. The adjustable suture locking apparatus of claim 1, wherein
the handle further comprises a movable portion, wherein the movable portion is able to move with respect to the fixing portion;
the lock pin defines a hollow inner cavity along an axial direction of the lock pin, wherein the hollow inner cavity is configured to receive the suture and allow the suture to pass through; and
the adjustable suture locking apparatus further comprises:
a squeezing assembly operable to hold and press the lock pin to deform the lock pin;
a mandrel having a distal end coupled to a proximal end of the squeezing assembly and a proximal end movably coupled to the movable portion; and
the squeezing assembly and the mandrel are both received in the receiving cavity, the movable portion is able to move with respect to the fixing portion to drive the mandrel to move, so as to enable the squeezing assembly to hold and press the lock pin.

8. The adjustable suture locking apparatus of claim 7, wherein the squeezing assembly comprises a collet and a pushing rod, wherein the collet comprises an upper clip, a lower clip, and a clip connecting portion disposed between a proximal end of the upper clip and a proximal end of the lower clip, wherein the lock pin is disposed between the upper clip and the lower clip, a proximal end of the pushing rod is coupled to the distal end of the mandrel, a distal end of the pushing rod is adjacent to the upper clip, and the mandrel drives the pushing rod to move toward the upper clip to push the upper clip toward the lower clip, so as to enable the upper clip and the lower clip to cooperatively hold and press the lock pin.

9. The adjustable suture locking apparatus of claim 8, wherein the upper clip has a first surface facing the lock pin, and the lower clip has a second surface facing the lock pin, wherein the first surface is provided with a first engaging portion, the second surface is provided with a second engaging portion, and the first engaging portion and the second engaging portion are able to be engaged with each other to enable the upper clip and the lower clip to be in a closed state.

10. The adjustable suture locking apparatus of claim 8, wherein
the distal end of the pushing rod has a first inclined surface inclined downwardly from the distal end of the pushing rod to the proximal end of the pushing rod; and
the upper clip has a second inclined surface facing away from the lock pin, wherein the second inclined surface is inclined downwardly from the distal end of the upper clip to the proximal end of the upper clip.

11. The adjustable suture locking apparatus of claim 10, wherein the first inclined surface has a smaller slope than the second inclined surface.

12. The adjustable suture locking apparatus of claim 7, wherein the hollow inner cavity has an upper surface and a lower surface opposite the upper surface, wherein a lock pad protrudes from the upper surface, the lower surface defines a concave lock hole, and the lock pad is adapted to the lock hole.

13. The adjustable suture locking apparatus of claim 7, wherein the outer tube defines a suture inlet at a distal end of the outer tube along a radial direction of the outer tube and a suture outlet, wherein the suture inlet has a diameter at least equal to a diameter of a portion of the lock pin, wherein the portion of the lock pin has a maximum outer diameter, wherein the suture inlet and the suture outlet both communicate with the hollow inner cavity of the lock pin.

14. The adjustable suture locking apparatus of claim 13, wherein the outer tube is provided with a holding portion at the distal end of the outer tube, wherein the holding portion has a diameter gradually decreasing from a proximal end of the holding portion to a distal end of the holding portion.

15. The adjustable suture locking apparatus of claim 14, wherein the holding portion has a holding portion end surface at the distal end of the holding portion, and the holding portion defines an opening along an axial direction of the holding portion, wherein the opening extends through the holding portion end surface and communicates with the receiving cavity.

16. The adjustable suture locking apparatus of claim 15, wherein the opening comprises a protrusion protruding along a radial direction of the opening, wherein the protrusion and the holding portion end surface define a preset distance, and the lock pin is partially disposed in the opening to enable the protrusion to fix the lock pin.

17. The adjustable suture locking apparatus of claim 16, wherein the lock pin is provided with a circular cone at the distal end of the lock pin, wherein the circular cone has a larger diameter than the proximal end of the lock pin and an arc-shaped inner sidewall, the circular cone is disposed in the opening, and the protrusion fixes the lock pin.

* * * * *